(12) United States Patent
Srivastava

(10) Patent No.: US 12,376,857 B2
(45) Date of Patent: Aug. 5, 2025

(54) DEVICE FOR MANUALLY PERFORMING ANASTOMOSIS

(71) Applicant: Sudhir Prem Srivastava, Haryana (IN)

(72) Inventor: Sudhir Prem Srivastava, Haryana (IN)

( * ) Notice: Subject to any disclaimer, the term of this patent is extended or adjusted under 35 U.S.C. 154(b) by 0 days.

(21) Appl. No.: 18/567,753

(22) PCT Filed: Apr. 21, 2023

(86) PCT No.: PCT/IN2023/050391
§ 371 (c)(1),
(2) Date: Dec. 6, 2023

(87) PCT Pub. No.: WO2023/238142
PCT Pub. Date: Dec. 14, 2023

(65) Prior Publication Data
US 2025/0090171 A1  Mar. 20, 2025

(30) Foreign Application Priority Data
Jun. 10, 2022 (IN) .............................. 202211033297

(51) Int. Cl.
*A61B 17/115* (2006.01)
*A61B 17/00* (2006.01)
*A61B 17/11* (2006.01)

(52) U.S. Cl.
CPC ... *A61B 17/115* (2013.01); *A61B 2017/00367* (2013.01); *A61B 2017/1107* (2013.01)

(58) Field of Classification Search
CPC ........ A61B 17/115; A61B 2017/00367; A61B 2017/1107
See application file for complete search history.

(56) References Cited

U.S. PATENT DOCUMENTS

| | | | | |
|---|---|---|---|---|
| 4,488,523 A | * | 12/1984 | Shichman | A61B 17/115 227/179.1 |
| 5,951,574 A | * | 9/1999 | Stefanchik | A61B 17/1285 606/143 |
| 7,211,092 B2 | * | 5/2007 | Hughett | A61B 17/068 606/143 |
| 7,278,563 B1 | * | 10/2007 | Green | A61B 17/07207 227/176.1 |

(Continued)

FOREIGN PATENT DOCUMENTS

| | | |
|---|---|---|
| CA | 2530141 A1 | 11/1995 |
| JP | 2004524078 A | 8/2004 |

*Primary Examiner* — Michelle Lopez
(74) *Attorney, Agent, or Firm* — SZDC Law PC

(57) ABSTRACT

The present invention relates to a device for manually performing anastomosis between a graft vessel and a target vessel in order to bypass the blocked in coronary artery to restore adequate blood flow to the heart muscle. The manually operated configuration of the anastomosis device includes a handle (105) positioned at its distal end and an end-effector assembly (101) positioned at its proximal end. A shaft (103) one end is coupled to the handle (105) and the shaft (103) other end is coupled to the end-effector assembly (101). Further, a cable (223) is positioned within the shaft (103), wherein the cable (223) one end is secured to the handle (105) and the cable (223) other end is secured to the end-effector assembly (101) and the cable (223) facilitates in actuation of the end-effector assembly (101) to perform anastomosis.

15 Claims, 9 Drawing Sheets

(56) References Cited

U.S. PATENT DOCUMENTS

| | | | |
|---|---|---|---|
| 2002/0143346 A1* | 10/2002 | McGuckin, Jr. | ............................ A61B 17/07207 606/151 |
| 2006/0085033 A1* | 4/2006 | Criscuolo | .......... A61B 17/1155 227/19 |
| 2013/0190753 A1 | 7/2013 | Garrison et al. | |
| 2021/0401431 A1* | 12/2021 | Murthy Aravalli Avvln | ............... A61B 17/07207 |
| 2022/0015767 A1* | 1/2022 | Williams | ........... A61B 17/1155 |

\* cited by examiner

DEVICE FOR MANUALLY PERFORMING ANASTOMOSIS

CROSS-REFERENCE TO RELATED APPLICATIONS AND PRIORITY

This application is the National stage application of International Application No. PCT/IN2023/050391 filed on Apr. 21, 2023, which application claims priority from Indian Patent Application No. 202211033297, filed on Jun. 10, 2022.

FIELD OF THE DISCLOSURE

The present invention generally relates to a surgical device, and more particularly, the invention relates to a device for manually performing anastomosis in a minimally invasive surgery.

BACKGROUND OF THE DISCLOSURE

This section is intended to introduce the reader to various aspects of art that may be related to various aspects of the present disclosure, which are described below. This disclosure is believed to be helpful in providing the reader with background information to facilitate a better understanding of the various aspects of the present disclosure. Accordingly, it should be understood that these statements are to be read in this light, and not just as admissions of prior art.

Anastomosis is a surgical procedure in which two blood vessel or arteries are joined together to form/restore a continuous blood flow channel. Anastomosis may be performed for treatment of various medical condition such as coronary artery diseases (CAD). When a patient suffers from (CAD), an occlusion or stenosis in a coronary artery restricts blood flow to the heart muscle. In order to treat CAD, the area where the occlusion occurs is bypassed to reroute blood flow by grafting a vessel in the form of a harvested artery or vein, or a prosthesis. Anastomosis is performed between a graft vessel and two target vessels in order to bypass the blocked coronary artery, circumvent the occlusion and restore adequate blood flow to the heart muscle. This treatment is known as a coronary artery bypass graft procedure (CABG).

In a CABG procedure, a graft vessel such as a saphenous vein, mammary artery, radial artery or other blood vessel is harvested from the patient or another source, then placed in a bowl or other container and immersed in saline, blood or other biocompatible liquid. Before that graft vessel is connected to the target vessels, it may be prepared in some way, such as by connecting it to an anastomosis device and/or a tool for applying the anastomosis device. The graft vessel is typically connected to the anastomosis device and/or tool manually by one or more people in the operating room, using forceps, tweezers and/or other tools. Substantial skill is required to connect the slippery graft vessel to the anastomosis device and/or tool without damaging the graft vessel or otherwise rendering it unusable.

In the conventional CABG, a large incision is made in the chest and the sternum is sawed in half to allow access to the heart. In addition, a heart lung machine is used to circulate the patient's blood so that the heart can be stopped and the anastomosis can be performed. In order to minimize the trauma to the patient induced by conventional CABG, less invasive techniques have been developed in which the surgery is performed through small incisions in the patient's chest with the aid of endoscope.

There exists an anastomosis device in the art which are used for performing the anastomosis. However, such anastomosis devices are complex to manufacture, costlier and difficult to use.

In the light of aforementioned challenges, there is a need for an improved manually operated anastomosis device that allows ease, safety, and less cost for performing anastomosis.

SUMMARY

An anastomosis device (100) to connect a graft vessel to a target vessel comprising a handle (105) positioned at a distal end of the anastomosis device (100), an end-effector assembly (101) positioned at a proximal end of the anastomosis device (100), a shaft (103), wherein the shaft (103) one end is coupled to the handle (105) and the shaft (103) other end is coupled to the end-effector assembly (101) and a cable (223) positioned within the shaft (103), wherein the cable (223) one end is secured to the handle (105) and the cable (223) other end is secured to the end-effector assembly (101) to facilitates in actuation of the end-effector assembly (101) to perform anastomosis.

The handle (105) of the anastomosis device (100) further comprises a plurality of actuation lever (205a), (205b) operationally connected to the cable (223) to facilitate in actuation of the end-effector assembly (101) to perform anastomosis. Further, a proximal end of the actuation lever (205a) is operationally secured by a screw (209a) and a distal end of the actuation lever (205a) is secured to a linkage (207a) and a proximal end of the actuation lever (205b) is operationally secured by a screw (209b) and a distal end of the actuation lever (205b) is secured to a linkage (207b).

The handle (105) of the anastomosis device (100) further comprises a plurality of springs (215a), (215b) to facilitate in clamping and unclamping of the end-effector assembly (101) to perform anastomosis. Furthermore, the handle (105) comprises a carriage (225) positioned to the bottom housing (203) and capable of moving along its longitudinal axis, wherein the carriage (225) includes at least a hole (227a) in which the proximal end of the cable (223) is secured by a cup point set screw (229a).

An anastomosis device (100) to connect a graft vessel to a target vessel comprising an anvil assembly (303) having a longitudinal axis and a cable (417) secured to a cartridge body (403) at one end and other end of the cable (417) is secured to a handle (105), wherein the cable (417) facilitates in actuating an end-effector assembly (101) to perform anastomosis. The cable (417) is crimped to the cartridge body (403) at a hole (427) and other end of the cable (417) is secured to a hole (227a) by a cup point set screw (229a) at a carriage (225).

The anvil assembly (303) further comprising a plurality of pockets (502) configured at its distal end, wherein a plurality of staple (413) is configured to deformed against the plurality of pocket (502). The anvil assembly (303) further comprises a knife (503) positioned at center of the anvil assembly (303) and a knife block (505) positioned at a rear end of the knife (503), wherein the knife block (505) facilitates in advancing the knife (503) along the longitudinal axis of the anvil assembly (303). The knife block (505) includes a spring finger (513) to position the knife (503) riding on a ramp (515).

An anastomosis device (100) to connect a graft vessel to a target vessel comprising a cartridge assembly (301) having a cartridge cap (401) and a cartridge body (403) and a cable (417) secured to a cartridge body (403) at one end and other end of the cable (417) is secured to a handle (105), wherein the cable (417) facilitates in actuating an end-effector assembly (101) to perform anastomosis. The cartridge cap (401) includes a plurality of flap tines (309) positioned at its distal end.

The cartridge body (403) includes at least a heel clip (307) positioned between the distal end and the proximal end of the cartridge body (403). Further, the cartridge body (403) comprises two arms (407a), (407b) at its distal end and the two arms (407a), (407b) includes a cartridge (409a), (409b) containing plurality of staple drivers (411) and plurality of staples (411). Furthermore, the cartridge body comprises a dual wedge (415), wherein the dual wedge (415) includes two legs (419a), (419b) and a distal end of the two legs (419a), (419b) includes a cam (421a), (421b) configured to facilitate the drivers (411) movement in vertically downward direction to push the staples (413) against the against the plurality of pocket (502) of the anvil assembly (303).

BRIEF DESCRIPTION OF THE DRAWINGS

The summary above, as well as the following detailed description of the disclosure, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

DETAILED DESCRIPTION OF THE DISCLOSURE

Figure 1:
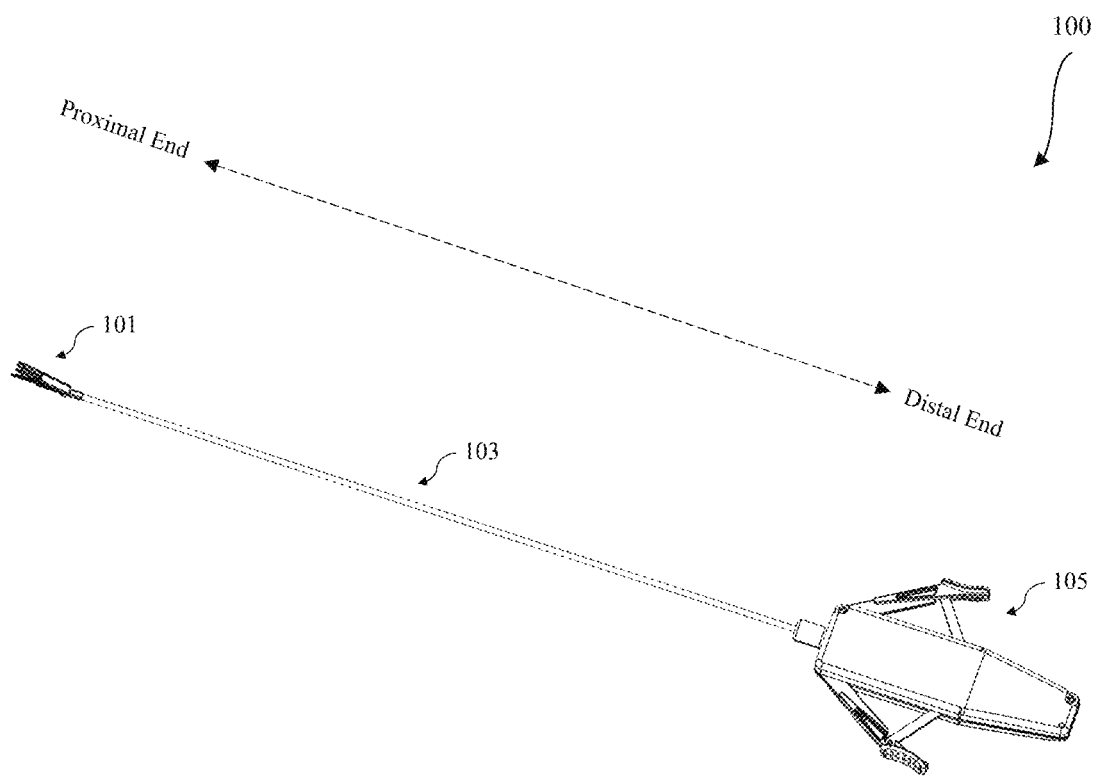
FIG. 1 illustrates a perspective view of a manually operated anastomosis device in accordance with an embodiment of the disclosure.

For the purpose of promoting an understanding of the principles of the disclosure, reference will now be made to the embodiment illustrated in the drawings and specific language will be used to describe the same. It will nevertheless be understood that no limitation of the scope of the disclosure is thereby intended, such alterations and further modifications in the illustrated system, and such further applications of the principles of the disclosure as illustrated therein being contemplated as would normally occur to one skilled in the art to which the disclosure relates.

It will be understood by those skilled in the art that the foregoing general description and the following detailed description are exemplary and explanatory of the disclosure and are not intended to be restrictive thereof. Throughout the patent specification, a convention employed is that in the appended drawings, like numerals denote like components.

Reference throughout this specification to "an embodiment", "another embodiment", "an implementation", "another implementation" or similar language means that a particular feature, structure, or characteristic described in connection with the embodiment is included in at least one embodiment of the present disclosure. Thus, appearances of the phrase "in an embodiment", "in another embodiment", "in one implementation", "in another implementation", and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures proceeded by "comprises . . . a" does not, without more constraints, preclude the existence of other devices or other sub-systems or other elements or other structures or additional devices or additional sub-systems or additional elements or additional structures.

Unless otherwise defined, all technical and scientific terms used herein have the same meaning as commonly understood by one of ordinary skill in the art to which this disclosure belongs. The device, system, and examples provided herein are illustrative only and not intended to be limiting.

The terms "a" and "an" herein do not denote a limitation of quantity, but rather denote the presence of at least one of the referenced items. Further, the term sterile barrier and sterile adapter denotes the same meaning and may be used interchangeably throughout the description.

Embodiments of the disclosure will be described below in detail with reference to the accompanying drawings.

The disclosure relates to a device for manually performing anastomosis between a graft vessel and a target vessel in order to bypass the blockage in coronary artery to restore adequate blood flow to the heart muscle. The anastomosis device is intended to create an end-to-side anastomosis between a graft vessel and a target vessel. The anastomosis is created by the delivery of staples that connect the graft vessel to the target vessel and the creation of an incision to open a flow path between the graft vessel and the target vessel. The manually operated configuration of the anastomosis device incorporates a handle for actuating end-effector by a shaft coupled to the handle and the end-effector.

As illustrated in FIG. 1, the anastomosis device (100) comprises a proximal end (101), a distal end (105) and a shaft (103) connecting the proximal end (101) to the distal end (105). The proximal end (101) may interchangeably be referred as an end-effector or end-effector assembly (101) throughout the description. The end-effector (101) is the actual part of the anastomosis device (100) which touches the graft vessel and the target vessel to perform anastomosis. The distal end (105) may be an actuation mechanism which facilitates the proximal end (101) in performing the anastomosis. The connecting shaft (103) may include a cable (not shown) to facilitate in performing the anastomosis by transmitting the actuation from distal end (105) to the proximal end (101). The connecting shaft may be made of a rigid material or a flexible material. The details of the distal end (101) and the proximal end (105) are disclosed in the forthcoming description.

Figure 2A:
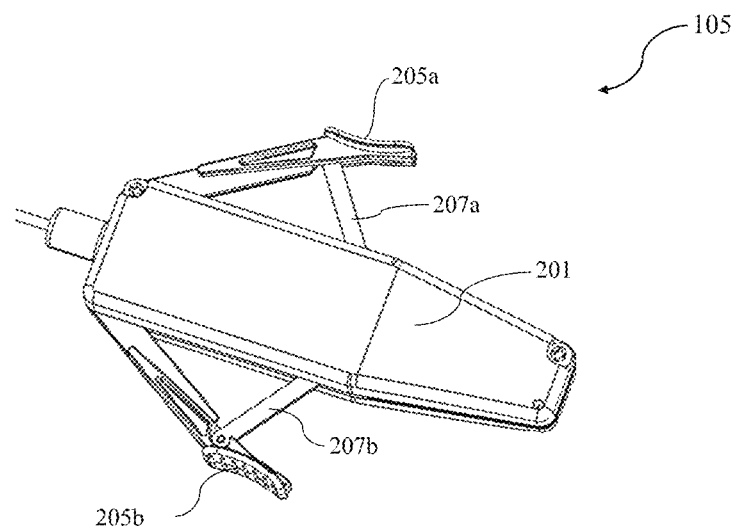
FIG. 2(a) illustrates a distal end of the manually operated anastomosis device in accordance with an embodiment of the disclosure.
Figure 2B:
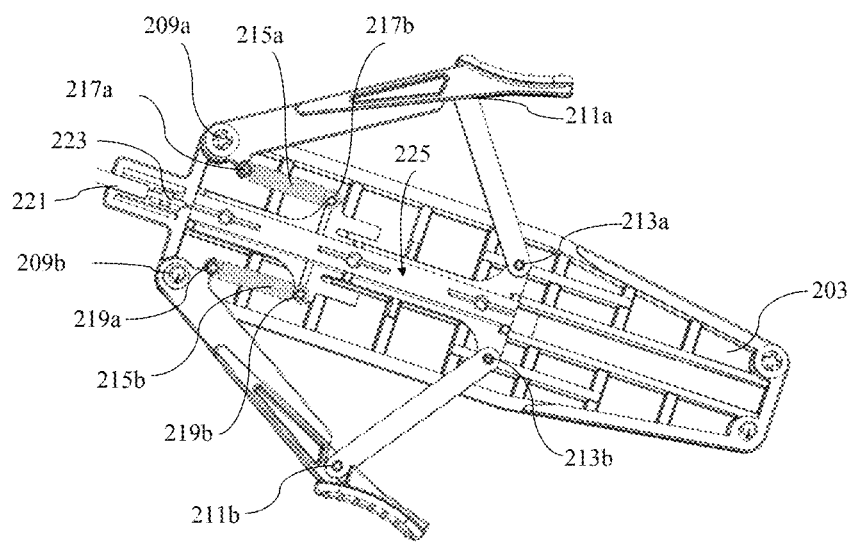
FIG. 2(b) illustrates the distal end of the manually operated anastomosis device without a housing in accordance with an embodiment of the disclosure.

As illustrated in FIG. 2(a) and FIG. 2(b), the distal end (105) includes a top housing (201) and a bottom housing (203). The distal end (105) is a hand held device including an actuation lever (205a), (205b) to actuate the proximal end/end-effector (101) to perform anastomosis. The distal end (105) may interchangeably be referred as handle (105). A proximal end of the actuation lever (205a) is secured to the bottom housing (203) by a securing means (209a) and a distal end of the actuation lever (205a) is secured to a proximal end of a linkage (207a) by a securing means (211a) (The securing means (211a) is not visible in the FIG. 2(b); however, it is same as securing means as shown by referral numeral (211b) in FIG. 2(b)). A distal end of the linkage (207a) is secured to a carriage assembly (225) by a securing means (213a). The securing means (213a) may be a lug (213a) protruding from a distal end of the carriage assembly (225). A proximal end of the actuation lever (205b) is secured to the bottom housing (203) by a securing means (209b) and a distal end of the actuation lever (205b) is secured to a proximal end of a linkage (207b) by a securing means (211b). A distal end of the linkage (207b) is secured to the carriage assembly (225) by a securing means (213b). The securing means (213b) may be a lug (213b) protruding from the distal end of the carriage assembly (225). The carriage assembly (225) is secured to the bottom housing (203) such that the carriage assembly (225) may be configured to move along the longitudinal axis of the bottom housing (203). Further, the securing means (209a), (209b) may be a screw which allows the proximal end of the actuation lever (205a), (205b) to rotate along the longitudinal axis of the screw.

Further, a plurality of springs (215a), (215b) is positioned at the bottom housing (203) to facilitate in the actuation mechanism of the proximal end/end-effector (101) of the anastomosis device (100). A proximal end of the spring (215a) is secured to a lug (217a) and the lug (217a) is protruding from the proximal end of the actuation lever (205a). The distal end of the spring (215a) is secured to a lug (217b) and the lug (217b) is protruding from the carriage (225). Accordingly, a proximal end of the spring (215b) is secured to a lug (217b) and the lug (217b) is protruding from the proximal end of the actuation lever (205b). The distal end of the spring (215b) is secured to a lug (219b) and the lug (219b) is protruding from the carriage (225).

According to an embodiment, the plurality of springs (215a), (215b) are in neutral position during the non-actuated state of the anastomosis device (100). In the actuated state (when the actuation levers (205a), (205b) are squeezed inwardly) of the anastomosis device (100), the springs (215a), (215b) may be in a stretched position.

Figure 2C:
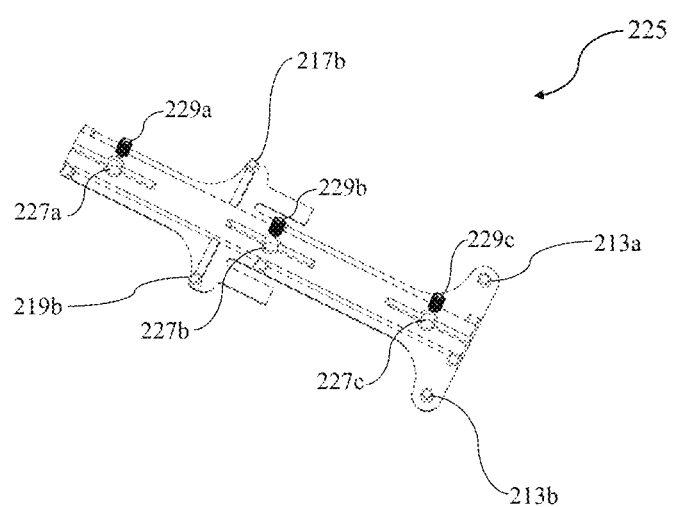
FIG. 2(c) illustrates a carriage assembly of the distal end of the manually operated anastomosis device without the housing in accordance with an embodiment of the disclosure.

FIG. 2(c) illustrates a carriage assembly of the distal end/handle (105) of the anastomosis device (100). The carriage assembly (225) is positioned at the bottom housing (203). The carriage assembly (225) comprises a plurality of holes on its longitudinal axis. In a specific embodiment, the carriage assembly (225) comprises three holes (227a), (227b) and (227c). A distal end of a cable (223) is secured to any of the three holes (227a), (227b) and (227c) on the carriage assembly (225) by means of any one of a plurality of securing means but not limited to cup point set screws (229a), (229b) and (229c). A shaft (221) is a hollow flexible tube through which the cable (223) enclosed. The shaft (221) connects the end-effector (101) and the handle (105). The proximal end of the cable (223) is secured to the end-effector (101) of the manually operated anastomosis device (100). In one implementation, the distal end of the cable (223) is fastened to the hole (227a) by the cup point set screw (229a) and in another implementation, the distal end of the cable (223) is fastened to the hole (227b) by the cup point set screw (229b) and in yet another implementation, the distal end of the cable (223) is fastened to the hole (227c) by the cup point set screw (229c). According to an embodiment, when the cable (223) is new, it may be fastened to the hole (227a) by the cup point set screw (229a). However, the cable (223) may develop a slackness upon multiple usage of the anastomosis device. Accordingly, to compensate the slackness in the cable (223), the cable (223) may be fastened to the hole (227b) or (227c) by the cup point set screw (229b) or (229c) respectively.

According to an embodiment, a medical practitioner such as doctor, nurse, medical assistant or any trained operating room assistant may use the manually operated anastomosis device (100) to perform anastomosis. The anastomosis device (100) is actuated by squeezing the actuation lever (205a), (205b) inwardly toward the housing. When the actuation lever (205a) and (205b) are squeezed inwardly, the proximal end of the actuation levers (205a) rotates around the longitudinal axis of the securing means (209a) and the proximal end of the actuation levers (205b) rotates around the longitudinal axis of the securing means (209b). Simultaneously, when the actuation lever (205a) and (205b) are squeezed inwardly, the distal end of the linkage (207a) rotates around the longitudinal axis of the lug (213a) and the distal end of the linkage (207b) rotates around the longitudinal axis of the lug (213b). The squeezing action of the actuation lever (205a), (205b) facilitate the movement of the carriage assembly (225) toward the distal end of the handle (105) and accordingly the cable (223) fastened to the carriage assembly also pulled toward the distal end of the handle (105) thereby the actuating the clamping of the end-effector (101) of the anastomosis device to perform anastomosis. The detailed explanation of clamping of the end-effector assembly (101) is explained in the description of subsequent figures.

Figure 3A:
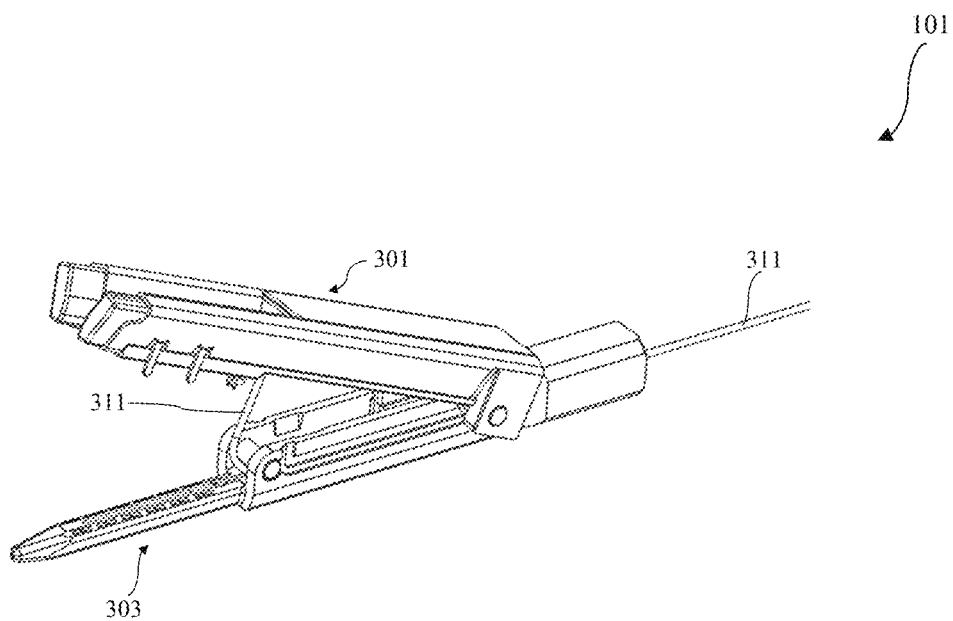
FIG. 3(a) illustrates a perspective view of a proximal end of the manually operated anastomosis device in accordance with an embodiment of the disclosure.
Figure 3B:
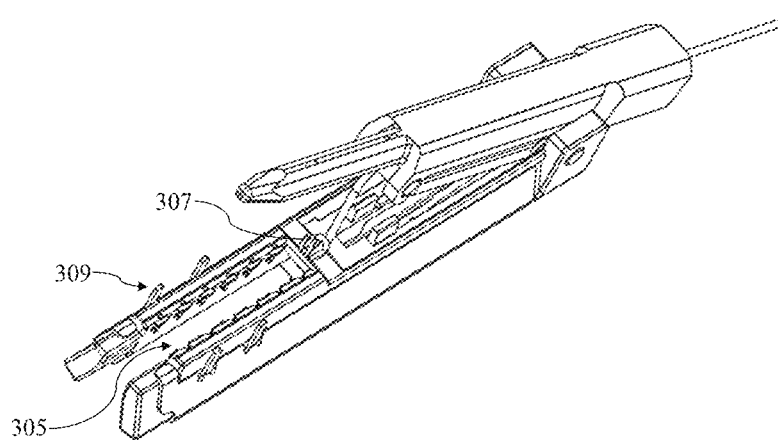
FIG. 3(b) illustrates another perspective view of the proximal end of the manually operated anastomosis device in accordance with an embodiment of the disclosure.

As illustrated in FIG. 3(a) and FIG. 3(b), the proximal end of the manually operated anastomosis device comprises a cartridge assembly (301) and an anvil assembly (303). The proximal end may also be referred as end-effector/end-effector assembly. The cartridge assembly (301) comprises plurality of staples and its driver's assembly (305), a heel clip (307) and a plurality of flap tines (309). An actuation cable (311) (the actuation cable (311) is same as cable (223) as shown in FIG. 2(b)) one end is secured to a distal end of the cartridge assembly (301) by means of various securing mechanism but not limited to crimping. The other end of the actuation cable (311) is secured to the distal end/handle (105) (as shown in FIG. 2(b)) of the manually operated anastomosis device.

According to one implementation, the method used for performing the anastomosis is to first prepare the graft vessel and mount it on the cartridge assembly (301). The graft vessel is prepared by creating a hood and the graft vessel is positioned between the arms (407a, 407b) (as shown in FIG. 4(b)) of the cartridge assembly (301) with an apex of the hood fitted onto the heel clip (307). The flaps of the hood are pressed onto the flap tines (309). The next step is to create a small incision in the target vessel. The anastomosis device is positioned and the anvil assembly (303) is inserted into the target vessel. The positioning of the end-effector assembly (101) after insertion into the target vessel is facilitated by grasping the end-effector assembly (101) on the proximal hub using a grasper or other suitable instrument. After insertion of the anvil assembly (303) into the target vessel, the anastomosis device is actuated by squeezing the actuation lever (205a, (205b) inwardly (as shown in FIG. 2(a)). First, the end-effector assembly (101) is clamped and this action clamps the anvil assembly (303) (inside the target vessel) to the cartridge assembly (301) (with the graft vessel mounted on it). Once the anvil assembly (303) is fully clamped with the cartridge assembly (301), the anastomosis device immediately proceeds with the deployment/forming of the staples facilitated by driver's and staple assembly (305) and the creation of the incision which opens the required flow path between the graft vessel and the target vessel. When the actuation is complete, the cartridge assembly (301) has moved to a position to permit automatic unclamping when the actuation force is relaxed by releasing the handle (105). Once the anvil assembly (303) and the cartridge assembly (301) are unclamped, the anvil assembly (303) can be withdrawn from the target vessel a suture is placed to stitch and close hole created by the anvil assembly (303).

Figure 4A:
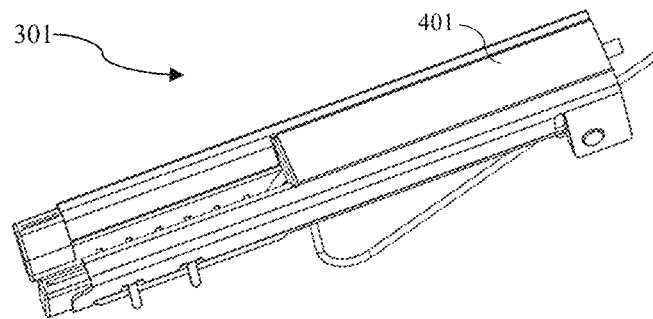
FIG. 4(a) illustrates a cartridge assembly of the proximal end of the manually operated anastomosis device in accordance with an embodiment of the disclosure.
Figure 4B:
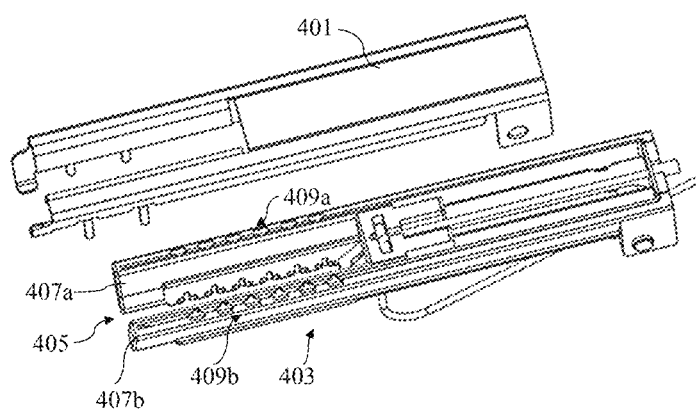
FIG. 4(b) illustrates an exploded view of the cartridge assembly of the proximal end of the manually operated anastomosis device in accordance with an embodiment of the disclosure.
Figure 4C:
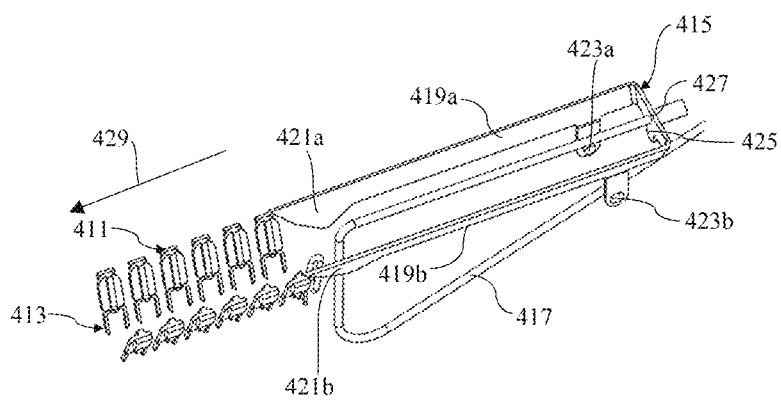
FIG. 4(c) illustrates an inside view of the cartridge assembly in accordance with an embodiment of the disclosure.
Figure 5A:
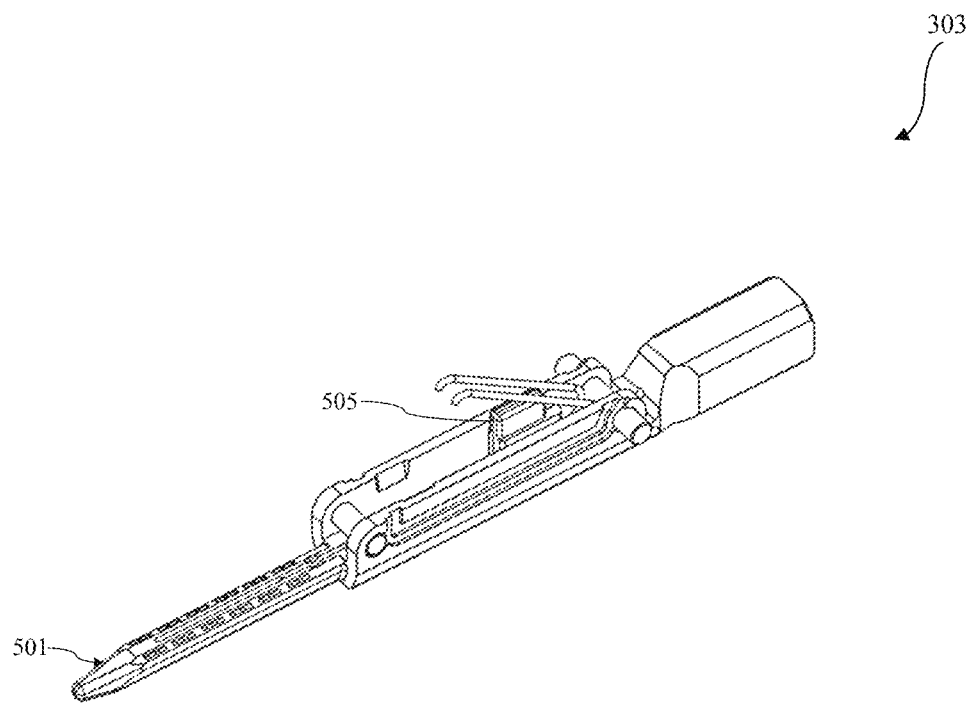
FIG. 5(a) illustrates an anvil assembly of the manually operated anastomosis device in accordance with an embodiment of the disclosure.
Figure 5B:
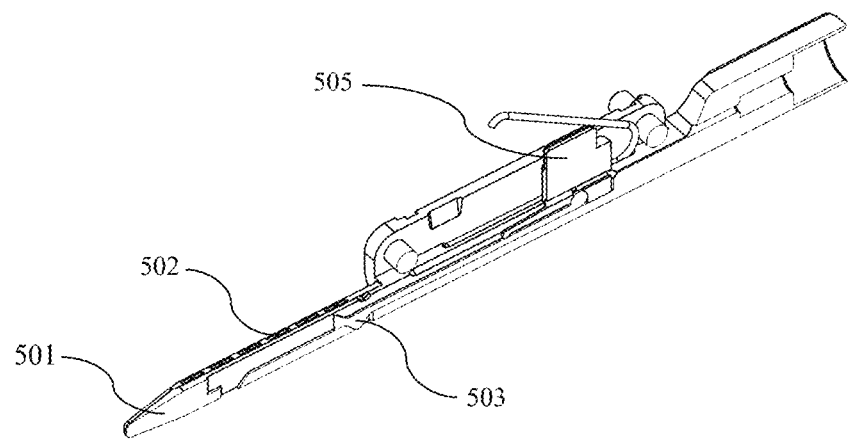
FIG. 5(b) illustrates a cross-sectional view of the anvil assembly of the manually operated anastomosis device in accordance with an embodiment of the disclosure.
Figure 5C:
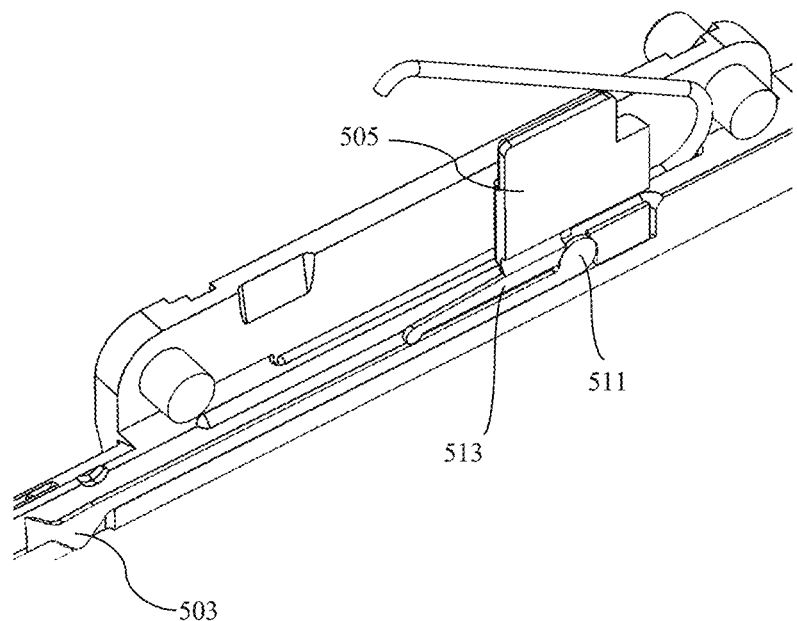
FIG. 5(c) illustrates a cross-sectional view of an initial position of a knife assembly of the anvil assembly in accordance with an embodiment of the disclosure.

As illustrated in FIG. 4(a), FIG. 4(b) and FIG. 4(c), the cartridge assembly (301) includes a cartridge cap (401) made up of any biocompatible materials. The cartridge assembly (301) further includes a cartridge body (403). The proximal end (405) of the cartridge body (403) includes two arms (407a), (407b) and each arm (407a), (407b) includes a bay/cartridge (409a), (409b) containing plurality of staple drivers (411) and plurality of staples (413). As illustrated in FIG. 4(c), the cartridge body (403) contains the plurality of staple drivers (411), plurality of staples (413) and a dual wedge (415). The cartridge assembly (301) has been designed to execute the required sequence of operation with the actuation of a cable (417). This is a significant simplification over other anastomosis devices which have four or more cables that are required. The plurality of staples (413) is used to connect the graft vessel to the target vessel. These staples (413) are arranged in bays/cartridges (409a), (409b) which are molded into both arms (407a), (407b) of the cartridge body (403). The staples (413) are formed against pockets (502) in the anvil assembly (303) as shown in FIG. 5(a) and FIG. 5(b). The staples (413) are advanced by individual drivers (411) one for each staple (413). The plurality of drivers (411) is sequentially actuated from right to left (as shown by the referral numeral 429) via a dual wedge (415). The dual wedge (415) has two legs (419a), (419b), one leg for each arm (409a), (409b) of the cartridges body (403). The one end of the dual wedge (415) includes a cam (421a), (421b) for moving the plurality of drivers (411) in downwardly to push the respective plurality staples (413) against the pocket (502) to perform the anastomosis.

The two legs (419a), (419b) of the dual wedge (415) includes a cam follower (423a), (423b) which facilitates in advancing the dual wedge (415) to facilitate the anastomosis. Further, the dual wedge (415) includes a cable hole (427) through which the one end of the actuation cable (417) is secured. The dual wedge (415) also includes an actuation tab (425) pointing in downwards direction which facilitate in advancing a knife block (505) (as shown in FIG. 5(b)) and which is explained in the description below.

Figure 5D:
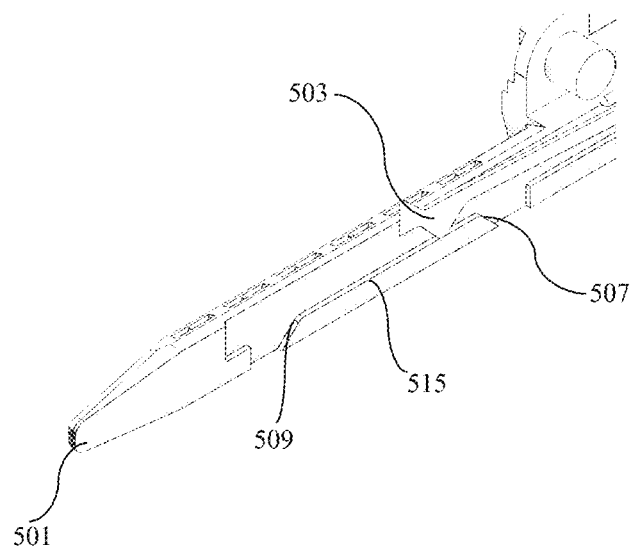
FIG. 5(d) illustrates a cross-sectional view of a cutting position of the knife assembly of the anvil assembly in accordance with an embodiment of the disclosure.

As illustrated in FIG. 5(a), FIG. 5(b), FIG. 5(c) and FIG. 5(d), the anvil assembly (303) includes a knife (503) and a knife block (505) for creating the incision in the target vessel that establishes the required flow path. The knife (503) is positioned within the anvil assembly (303) for creating the incision in the target vessel. The initial position of the knife (503) is retracted for easy insertion of the anvil (501) into the target vessel. As the staples (413) are formed, the knife (503) advances on a ramped surface (507) (as shown in FIG. 5(d)) to cutting the target vessel. Just prior to the end of stroke, the knife (503) moves down a ramp back (509) to the retracted position within the anvil for ease of removal. The other end which is opposite to the cutting end of the knife (503) has circular/oval profile (511). The circular/oval profile (511) of the knife (503) is positioned on a knife block (505). The knife block (505) has a spring finger (513) to keep the knife (503) riding on the ramp (515). Now, referring to FIG. 4(c), the knife block (505) is advanced when the actuation tab (425) on the dual wedge (415) engages it and pushes it in forward direction. Specifically, the dual wedge (415) actuation tab (425) is behind the knife block (505) initially. As the dual wedge (415) advances forward, the first staple (413) is formed. Then the actuation tab (413) of the dual wedge (415) engages the knife (503) so that the cut is initiated after the first staple (413) is formed. Similarly, as the dual wedge (415) continues forward, the knife (503) continues to cut the tissue just proximal of the next forming staple. Finally, the knife (503) is retracted on the ramp (509) as the last staple is formed. The result is a cut that begins just distal of the first formed staple and stops just proximal of the last formed staple.

Figure 6A:
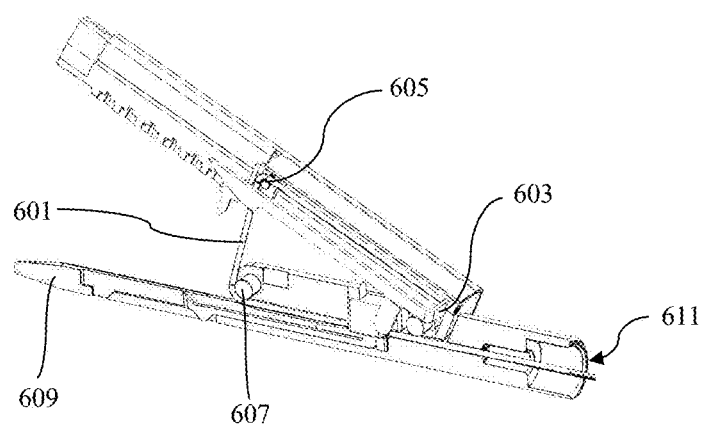
FIG. 6(a) illustrates a cross-section view of the anvil assembly and the cartridge assembly depicting initial position of clamping in accordance with an embodiment of the disclosure.
Figure 6B:
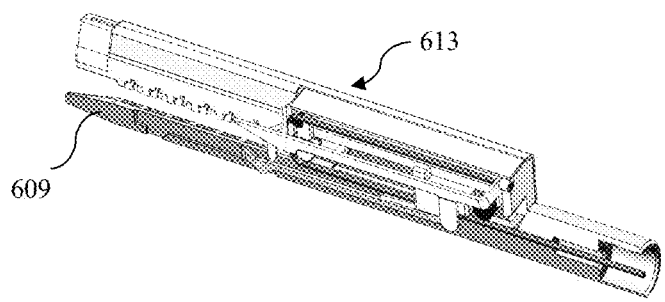
FIG. 6(b) illustrates the cross-section view of the anvil assembly and the cartridge assembly depicting clamped position in accordance with an embodiment of the disclosure.
Figure 6C:
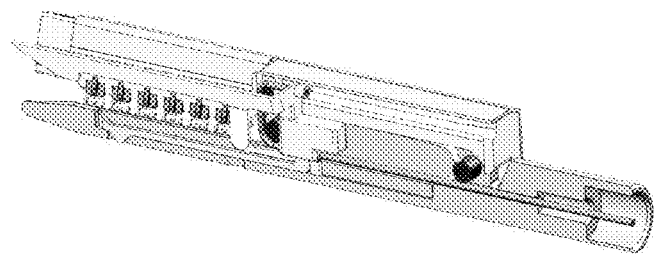
FIG. 6(c) illustrates the cross-section view of the anvil assembly and the cartridge assembly depicting final clamped position in accordance with an embodiment of the disclosure.

As illustrated in FIG. 6(a), FIG. 6(b) and FIG. 6(c), in order to activate the anastomosis device with a cable (601), the design takes advantage of the fact that clamping of anvil assembly (303) and the cartridge assembly (301) always precedes the dual wedge (603) advancing. The single deployment cable (601) is attached to the one end of the dual wedge (603). The cable (601) is routed from the dual wedge (603) around a first guide pin (605) and down to a second guide pin (607) on the anvil (609) and then routed out from the rear end (611). In order to ensure that the dual wedge (603) does not advance when the cable (601) is pulled until the anvil (609) and cartridge assembly (613) are clamped as shown in FIG. 6(b), legs with cam posts (423a), (423b) (as shown in FIG. 4(c)) are provided on both sides of the dual wedge (603).

Figure 7A:
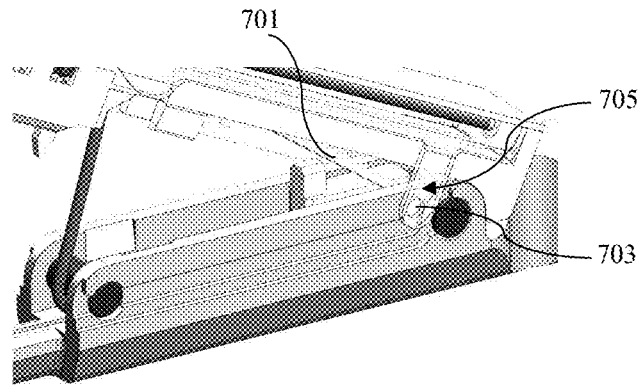
FIG. 7(a) illustrates a dual wedge cam follower assembly depicting initial position of clamping in accordance with an embodiment of the disclosure.
Figure 7B:
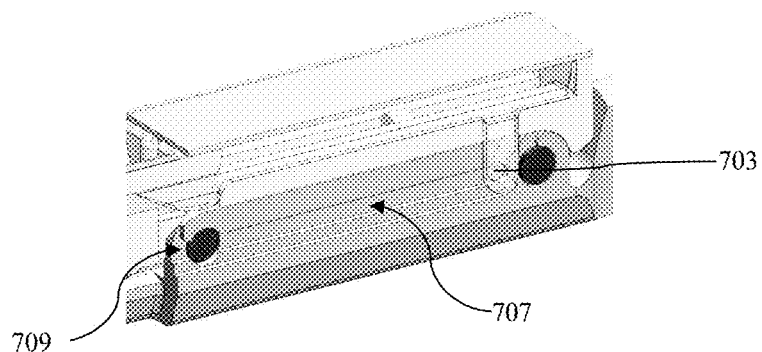
FIG. 7(b) illustrates the dual wedge cam follower assembly depicting clamped position in accordance with an embodiment of the disclosure.
Figure 7C:
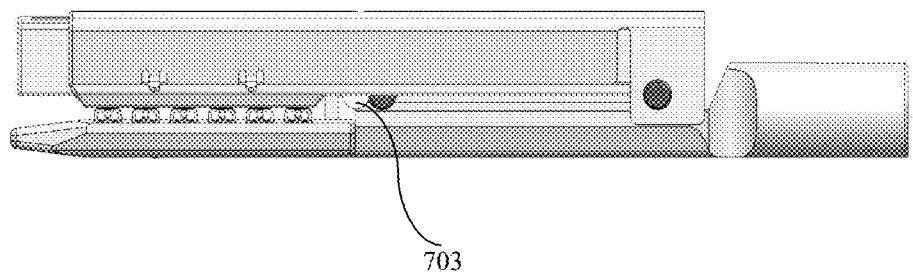
FIG. 7(c) illustrates the dual wedge cam follower assembly depicting final clamped position in accordance with an embodiment of the disclosure.

Referring to FIG. 7(a), FIG. 7(b) and FIG. 7(c), initially, when the anvil (609) and cartridge assembly (613) (as shown in FIG. 6(a)) are unclamped (due to a leaf spring (701) that forces them open), a dual wedge cam follower (703) are in a track (705) that only permits rotation of the dual wedge cam follower (703) as required for clamping. Once fully clamped, the dual wedge cam follower (703) aligns with a new section of horizontal track (707) that allows the dual wedge cam follower (703) to advance along the horizontal track (707). Once the dual wedge cam follower (703) gets to the final distal position, the cam path opens up again allowing the dual wedge cam follower (703) (and cartridge) to rotate back to the unclamped position (709).

The foregoing descriptions of exemplary embodiments of the present disclosure have been presented for purposes of illustration and description. They are not intended to be exhaustive or to limit the disclosure to the precise forms disclosed, and obviously many modifications and variations are possible in light of the above teaching. The exemplary embodiment was chosen and described in order to best explain the principles of the disclosure and its practical application, to thereby enable others skilled in the art to best utilize the disclosure and various embodiments with various modifications as are suited to the particular use contemplated. It is understood that various omissions, substitutions of equivalents are contemplated as circumstance may suggest or render expedient but is intended to cover the application or implementation without departing from the spirit or scope of the claims of the present disclosure.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

While specific language has been used to describe the disclosure, any limitations arising on account of the same are not intended. As would be apparent to a person in the art, various working modifications may be made to the device in order to implement the inventive concept as taught herein.

I claim:

1. An anastomosis device (100) to connect a graft vessel to a target vessel, the anastomosis device (100) comprising:
    a handle (105) positioned at a distal end of the anastomosis device (100);
    an end-effector assembly (101) positioned at a proximal end of the anastomosis device (100);
    a shaft (103), wherein the shaft (103) one end is coupled to the handle (105) and the shaft (103) other end is coupled to the end-effector assembly (101); and
    a cable (223) positioned within the shaft (103), wherein the cable (223) one end is secured to the handle (105) and the cable (223) other end is secured to the end-effector assembly (101) to facilitates in actuation of the end-effector assembly (101) to perform anastomosis,
    wherein the handle (105) further comprises a carriage (225) positioned to the bottom housing (203) and capable of moving along its longitudinal axis, wherein the carriage (225) includes at least a hole (227a) in which the proximal end of the cable (223) is secured by a cup point set screw (229a).

2. The anastomosis device (100) as claimed in claim 1, the handle (105) further comprises a plurality of actuation lever (205a), (205b) operationally connected to the cable (223) to facilitate in actuation of the end-effector assembly (101) to perform anastomosis.

3. The anastomosis device (100) as claimed in claim 2, wherein a proximal end of the actuation lever (205a) is operationally secured by a screw (209a) and a distal end of the actuation lever (205a) is secured to a linkage (207a).

4. The anastomosis device (100) as claimed in claim 2, wherein a proximal end of the actuation lever (205b) is operationally secured by a screw (209b) and a distal end of the actuation lever (205b) is secured to a linkage (207b).

5. The anastomosis device (100) as claimed in claim 1, the handle (105) further comprises a plurality of springs (215a), (215b) to facilitate in clamping and unclamping of the end-effector assembly (101) to perform anastomosis.

6. An anastomosis device (100) to connect a graft vessel to a target vessel, the anastomosis device (100) comprising:
    an anvil assembly (303) having a longitudinal axis, wherein the anvil assembly (303) comprises a knife (503) positioned at center of the anvil assembly (303); and
    a cable (417) secured to a cartridge body (403) at one end and other end of the cable (417) is secured to a handle (105), wherein the cable (417) facilitates in actuating an end-effector assembly (101) to perform anastomosis,
    wherein the cable (417) is crimped to the cartridge body (403) at a hole (427) and other end of the cable (417) is secured to a hole (227a) by a cup point set screw (229a) at a carriage (225).

7. The anastomosis device (100) as claimed in claim 6, the anvil assembly (303) further comprising a plurality of pockets (502) configured at its distal end.

8. The anvil assembly (303) as claimed in claim 7, wherein a plurality of staple (413) is configured to deformed against the plurality of pocket (502).

9. The anastomosis device (100) as claimed in claim 6, the anvil assembly (303) further comprising a knife block (505) positioned at a rear end of the knife (503), wherein the knife block (505) facilitates in advancing the knife (503) along the longitudinal axis of the anvil assembly (303).

10. The anvil assembly (303) as claimed in claim 9, wherein the knife block (505) includes a spring finger (513) to position the knife (503) riding on a ramp (515).

11. An anastomosis device (100) to connect a graft vessel to a target vessel, the anastomosis device (100) comprising: a cartridge assembly (301) having a cartridge cap (401) and a cartridge body (403); and a cable (417) secured to the cartridge body (403) at one end and other end of the cable (417) is secured to a handle (105), wherein the cable (417) facilitates in actuating an end effector assembly (101) to perform anastomosis,
wherein the cartridge cap (401) includes a plurality of flap tines (309) positioned at its distal end.

12. The anastomosis device (100) as claimed in claim 11, wherein the cartridge body (403) includes at least a heel clip (307) positioned between the distal end and the proximal end of the cartridge body (403).

13. The anastomosis device (100) as claimed in claim 11, the cartridge body (403) further comprises two arms (407*a*), (407*b*) at its distal end and the two arms (407*a*), (407*b*) includes a cartridge (409*a*), (409*b*) containing plurality of staple drivers (411) and plurality of staples (411).

14. The anastomosis device (100) as claimed in claim 11, the cartridge body further comprises a dual wedge (415), wherein the dual wedge (415) includes two legs (419*a*), (419*b*).

15. The dual wedge (415) as claimed in claim 14, wherein a distal end of the two legs (419*a*), (419*b*) includes a cam (421*a*), (421*b*) configured to facilitate the drivers (411) movement in vertically downward direction to push the staples (413) against the against the plurality of pocket (502) of the anvil assembly (303).

* * * * *